(12) United States Patent
Wasserfall et al.

(10) Patent No.: US 10,022,440 B2
(45) Date of Patent: Jul. 17, 2018

(54) MATERIALS AND METHODS FOR MODULATING IMMUNE RESPONSES

(75) Inventors: Clive Henry Wasserfall, Gainesville, FL (US); Mark A. Atkinson, Gainesville, FL (US); Benjamin George Keselowsky, Gainesville, FL (US); Young Mee Yoon, Gainesville, FL (US)

(73) Assignee: UNIVERSITY OF FLORIDA RESEARCH FOUNDATION, INCORPORATED, Gainesville, FL (US)

( * ) Notice: Subject to any disclaimer, the term of this patent is extended or adjusted under 35 U.S.C. 154(b) by 1135 days.

(21) Appl. No.: 14/117,122

(22) PCT Filed: Jun. 25, 2012

(86) PCT No.: PCT/US2012/043993
§ 371 (c)(1),
(2), (4) Date: Aug. 14, 2014

(87) PCT Pub. No.: WO2012/178160
PCT Pub. Date: Dec. 27, 2012

(65) Prior Publication Data
US 2015/0147388 A1 May 28, 2015

Related U.S. Application Data

(60) Provisional application No. 61/500,445, filed on Jun. 23, 2011.

(51) Int. Cl.
| | | |
|---|---|---|
| *A61K 39/00* | (2006.01) | |
| *A61K 47/00* | (2006.01) | |
| *A61K 39/39* | (2006.01) | |
| *A61K 39/35* | (2006.01) | |
| *A61K 38/19* | (2006.01) | |
| *A61K 47/34* | (2017.01) | |

(52) U.S. Cl.
CPC ............ *A61K 39/39* (2013.01); *A61K 38/193* (2013.01); *A61K 39/0005* (2013.01); *A61K 39/35* (2013.01); *A61K 47/34* (2013.01); *A61K 2039/55555* (2013.01); *A61K 2039/55561* (2013.01)

(58) Field of Classification Search
None
See application file for complete search history.

(56) References Cited

U.S. PATENT DOCUMENTS

2003/0003133 A1  1/2003  Schneider
2008/0233155 A1*  9/2008  Moingeon ............ A61K 39/35
424/275.1

FOREIGN PATENT DOCUMENTS

| WO | 2006/123230 | * 11/2006 | ............ A61K 39/39 |
| WO | WO 2007/063421 A2 | 6/2007 | |
| WO | WO 2010/132867 A1 | 11/2010 | |
| WO | WO 2011/014871 A1 | 2/2011 | |

OTHER PUBLICATIONS

Roep et al. 'Antigen Targets of Type 1 Diabetes Autoimmunity.' Cold Spring Harb Perspect Med 2012;2:a007781.*
Ali, Omar A. et al., "Infection-mimicking materials to program dendritic cells in situ," *Nature Materials*, Feb. 2009, vol. 8, p. 151-158.
Chou, Ho-Yuan et al., "Hydrogel-Delivered GM-CSF Overcomes Nonresponsiveness to Hepatitis B Vaccine through the Recruitment and Activation of Dendritic Cells," *The Journal of Immunology*, Oct. 2010, vol. 185, p. 5468-5475.
Hori, Yuki et al., "Injectable dendritic cell-carrying alginate gels for immunization and immunotherapy," *Biomaterials*, 2008, vol. 29, p. 3671-3682.
Keselowsky, Benjamin G. et al., "Multifunctional dendritic cell-targeting polymeric microparticles," *Human Vaccines*, Jan. 2011, vol. 7, No. 1, p. 37-44.
Okamoto, Noriaki et al., "Artificial lymph nodes induce potent secondary immune responses in naïve and immunodeficient mice," *The Journal of Clinical Investigation*, Apr. 2007, vol. 117, No. 4, p. 997-1007.
Singh, Ankur et al., "Efficient Modulation of T-cell Response by Dual-mode, Single-carrier Delivery of Cytokine-targeted siRNA and DNA Vaccine to Antigen-presenting Cells," *Molecular Therapy*, Dec. 2008, vol. 16, No. 12, p. 2011-2021.
Singh, Ankur et al., "in-situ crosslinking hydrogels for combinatorial delivery of chemokines and siRNA-DNA carrying microparticles to dendritic cells," *Biomaterials*, 2009, vol. 30, No. 28, 5187-5200.
Yoon, Young Mee et al., "Development of a Tolerogenic Matric Containing Autoantigens for the Prevention of Type 1 Diabetes," *Diabetes*, Jul. 2011, vol. 60, No. Suppl. 1, 2537-PO, p. A668-A669, Abstract.

* cited by examiner

*Primary Examiner* — Nora Rooney
(74) *Attorney, Agent, or Firm* — Saliwanchik, Lloyd & Eisenschenk

(57) ABSTRACT

The present invention provides materials and methods for modulating an immune response. In one embodiment, the present invention provides an initial artificial lymph-node homing environment, and a simultaneous, or subsequent, artificial spleen environment leading to the resolution of the activated immune responses. In one specific embodiment, the present invention can be used to prevent and/or treat pathogenic infection, cancer, allergenic reactions, and/or unwanted immune or auto-immune responses.

6 Claims, 1 Drawing Sheet

MATERIALS AND METHODS FOR MODULATING IMMUNE RESPONSES

CROSS REFERENCE TO A RELATED APPLICATION

This application is a National Stage Application of International Application Number PCT/US2012/043993, filed Jun. 25, 2012; which claims the benefit of U.S. Provisional Application Ser. No. 61/500,445, filed Jun. 23, 2011; which are incorporated herein by reference in their entirety.

The Sequence Listing for this application is labeled "Seq-List_ST25.txt", which was created on Jun. 22, 2012, and is 3 KB. The entire content is incorporated herein by reference in its entirety.

BACKGROUND OF INVENTION

While there have been some remarkable successes and advances in the vaccination field since Edward Jenner's observation that cowpox exposure protected against smallpox, there remain great challenges to achieving protective immunity against many infectious agents and pathological conditions.

In general, a vaccine is a biological preparation that improves immunity to a particular disease. A vaccine typically contains an agent that resembles a disease-causing entity. The agent stimulates the body's immune system to recognize the agent as foreign, destroy it, and "remember" it, so that the immune system can more easily recognize and destroy any such pathogen that it later encounters.

Vaccines can be prophylactic (e.g. to prevent or ameliorate the effects of a future infection by any natural or "wild" pathogen), or therapeutic (e.g. vaccines against cancer are also being investigated; see cancer vaccine).

For immunization against cancer and pathogenic infections, conventional vaccine design focuses on, primarily, the induction of "pro-inflammatory" responses.

On the other hand, for therapy of autoimmune diseases, the prevailing concept for autoantigen vaccination is tolerance induction. However, the present use of dendritic cell-based vaccines for treatment of type 1 diabetes suffers from several limitations. For instance, dendritic cell-based vaccine requires ex vivo modification of patients' cells and introducing the modified cells into patients. Unfortunately, this approach not only adversely affects patient safety, but is also associated with high cost. In addition, the present dendritic cell-based vaccine compositions have suboptimal ex vivo stability.

Thus, there is a need for developing improved vaccine techniques and compositions for the prevention and/or treatment of infection, cancer, and autoimmune diseases. Also, there is a need for improved materials and methods for programming and modifying immune cells directly in patients' body. As will be clear from the disclosure that follows, these and other benefits are provided by the present invention.

BRIEF SUMMARY

The present invention provides materials and methods for modulating an immune response. In one embodiment, the present invention provides an artificial lymph-node environment, and a simultaneous, or subsequent, artificial spleen environment. Advantageously, providing these environments leads to an effective resolution of the immune response.

In a specific embodiment, the materials and methods of the present invention can be used to prevent and/or treat pathogenic infections, cancer, allergenic reactions, and/or immune or auto-immune disorders.

In one embodiment, the present invention provides a device for modulating immune responses, wherein the device comprises a scaffold matrix made of biocompatible materials, wherein the scaffold matrix encapsulates therein, at least, a pro-inflammatory agent, an anti-inflammatory agent, and, optionally, an antigen, autoantigen, or allergen. In a specific embodiment, the immuno-modulating device of the invention is formulated as a vaccine.

In one embodiment, the scaffold matrix encapsulates therein a microparticle, wherein the outer surface of the microparticle comprises one or more surface ligands that bind to a target immune cell, and the microparticle encapsulates therein at least an antigen, autoantigen, or allergen.

In a specific embodiment, the scaffold matrix further comprises a chemoattractant. The chemoattractant can be selected from, for example, granulocyte macrophage colony stimulating factor (GM-CSF), granulocyte-colony stimulating factor (G-CSF), or both. In a specific embodiment, the scaffold material is a hydrogel. In one embodiment, the microparticle is made of poly(lactic-co-glycolic acid) (PLGA).

Another aspect of the present invention provides a method for modulating an immune response. In one embodiment, the method comprises administering, to a subject in need of such modulation, a pro-inflammatory adjuvant and an anti-inflammatory adjuvant, wherein the method further comprises administering an antigen, autoantigen or allergen, and, optionally, an immuno-modulating molecule that induces the migration of an immune cell.

In one embodiment, the immune modulation is achieved by programming immune cells (e.g., antigen-presenting cells) in situ. Antigen-presenting cells including, but not limited to, dendritic cells, macrophages and B cells, can be recruited to a device of the present invention, and activated to present to T cells, antigens, autoantigens or allergens on their surfaces (antigen priming); the programmed immune cells then migrate out of the device to downstream lymph nodes.

BRIEF DESCRIPTION OF SEQUENCES

Figure 1:
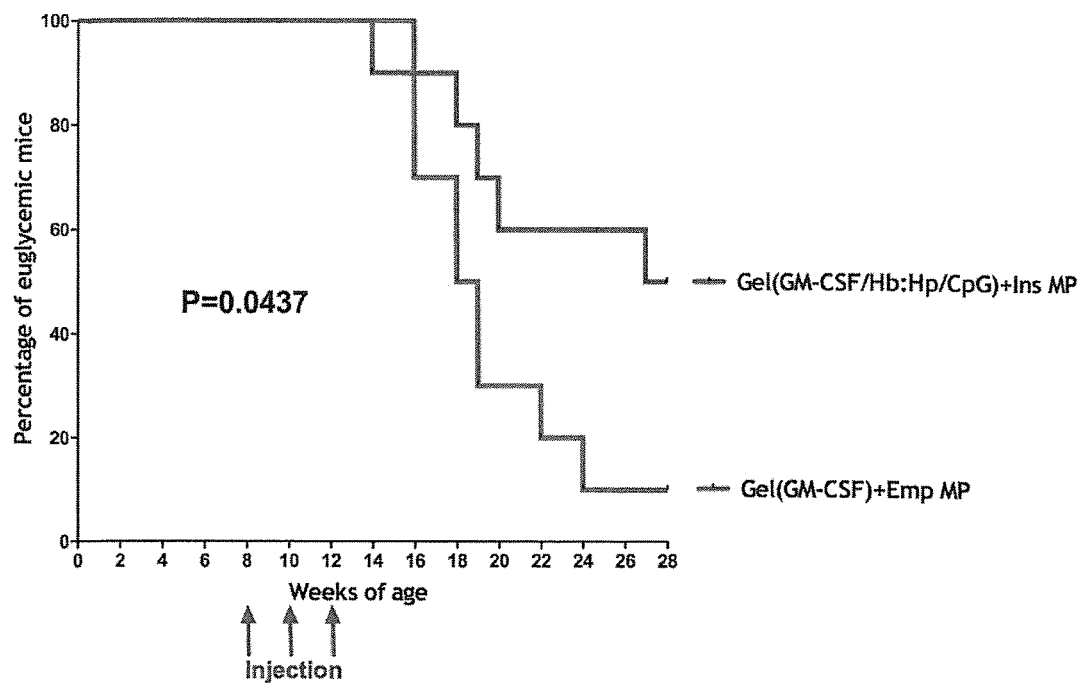
FIG. 1 shows Kaplan-Meier plots of diabetes incidence after subcutaneous injections of both pro- and anti-inflammatory adjuvants. It can be seen that the injections resulted in the prevention of diabetes (n=10/group, p=0.0437).

SEQ ID NO:1 is an amino acid sequence of a human granulocyte macrophage colony stimulating factor (GM-CSF) polypeptide useful according to the present invention.

SEQ ID NO:2 is an amino acid sequence of a human granulocyte-colony stimulating factor (G-CSF) polypeptide useful according to the present invention.

DETAILED DISCLOSURE

The present invention provides materials and methods for modulating immune responses. In one embodiment, the present invention delivers, to a subject, an initial immune activation signal, and a simultaneous, or subsequent, signal to dampen the activated immune response, thereby leading to effective modulation and resolution of an immune response.

Specifically, in one embodiment, the present invention provides an artificial lymph-node environment, and a simultaneous, or subsequent, artificial spleen environment leading to an effective and efficient resolution of immune responses. In specific embodiments, the present invention provides a protective immune response against pathogenic infection and/or cancer. In other embodiments, the present invention can be used to reduce allergenic reactions, and/or unwanted auto-immune responses.

In various embodiments, the present invention provides an antigen (associated with an infectious disease or cancer), an autoantigen (associated with an autoimmune disease), or an allergen (associated with an allergy) in a prime-boost design that follows a unique immune system modulation course. In a specific embodiment, the "prime" phase is achieved by the administration of a pro-inflammatory adjuvant, while the "boost" phase is achieved by the administration of an anti-inflammatory adjuvant.

In one embodiment, the pro-inflammatory adjuvant provides a lymph-node-type environment that activates pro-inflammatory pathways, such as the arachidonic acid/cyclooxygenase (COX) pathway. Exemplary pro-inflammatory adjuvants useful according to the present invention include, but are not limited to, aluminum hydroxide (Alum), lipopolysaccharides (LPS), cytosine-guanosine (CpG) oligonucleotide (CpG-ODN) sequences, and polyinosinic:polycytidylic acid (poly IC).

In one embodiment, the anti-inflammatory adjuvant provides a spleen-type environment that activates anti-inflammatory pathways, such as, for example, the hemeoxygenase-1 (HO-1) pathway. Exemplary pro-inflammatory adjuvants useful according to the present invention include, but are not limited to, hemoglobin:haptoglobin, hemin, heme:hemopexin, nonsteroidal anti-inflammatory drugs (NSAIDs), and triterpinoids.

In one embodiment, the administration of the pro-inflammatory adjuvant provides an artificial high-fat/low-hemoglobin environment that activates pro-inflammatory pathways, such as, for example, the arachidonic acid/cyclooxygenase (COX) pathway. This activation of the COX pathway can produce prostaglandins and leukotrienes and, thus, drives the acute phase of the immune response.

The administration of an anti-inflammatory adjuvant provides a low-fat/high-hemoglobin spleen-type environment that activates anti-inflammatory pathways, such as the hemeoxygenase-1 (HO-1) pathway. The activation of hemeoxygenase-1 results in the production of anti-inflammatory molecules, such as IL-10, carbon monoxide, and biliverdin. Biliverdin can be further broken down to bilirubin. Advantageously, upon the resolution of the inflammatory responses activated by the pro-inflammatory adjuvant and antigen, autoantigen, or allergen, immune cells acquire memory for the antigen, autoantigen, or allergen.

The present invention also provides a device for modulating an immune response in a subject. In one embodiment, the device comprises a scaffold matrix made of a biocompatible material. In a preferred embodiment, the scaffold matrix entraps a pro-inflammatory agent, an anti-inflammatory agent, and an antigen, autoantigen, or allergen. In one embodiment, the present invention provides an "all-in-one" device that creates an artificial lymph node and spleen "dual-environment," thereby increasing the efficiency and efficacy of vaccination.

In a specific embodiment, the device comprises an injectable hydrogel, wherein the hydrogel further comprises a chemoattractant that directs dendritic cells and T cells to the site of injection, pro-inflammatory and/or anti-inflammatory adjuvants that act extracellularly on the recruited immune cells, and microparticles, wherein the microparticles encapsulate therein, at least, an antigen, autoantigen, or allergen, and, optionally, additional adjuvants and therapeutic agents. In one embodiment, the immune cells (such as dendritic cells) phagocytose the microparticles; as a result, agents (such as antigens, autoantigen or allergens, and additional adjuvants) encapsulated in the microparticles can be delivered intracellularly into the immune cells.

Thus, in one embodiment, the present invention provides an immuno-modulating device, comprising a hydrogel-based scaffold matrix that comprises: a) chemoattractants; b) adjuvants; and c) microparticles (for example, made of PLGA) encapsulating, at least, an antigen, autoantigen, or allergen.

The immuno-modulating device can provide timed release of adjuvants, chemoattractants, antigen, autoantigen, or allergen, and, optimally, additional therapeutic agents. In one embodiment, the microparticle size allows the immune cells to phagocytose the micoparticle and the outer surface of the microparticle can further comprise one or more surface ligands or surface antibodies that target specific immune cells.

Device for Modulating Immune Responses

The subject invention provides a device for modulating an immune response in a subject. In one embodiment, the device comprises a scaffold matrix made of a biocompatible material, wherein the scaffold matrix encapsulates therein a pro-inflammatory agent, an anti-inflammatory agent, and, optionally, an antigen, autoantigen, or allergen. The anti-inflammatory agent can be released after the pro-inflammatory agent is released or the anti-inflammatory agent and the pro-inflammatory agent can be released simultaneously.

Biocompatible scaffold materials useful according to the present invention include, but are not limited to, hydrogel, collagen, alginate, poly(glycolide) (PGA), poly(L-lactide) (PLA), poly(lactide-co-glycolide) (PLGA), and polyethylene glycol (PEG).

In one embodiment, the scaffold matrix is made of materials comprising a hydrogel. The hydrogel of the present invention can be made of one or more hydrogel-forming polymers selected from, for example, vinyl sulfone, acryl-derivatized polysaccharide, thiol-derivatized polysaccharide, acryl-derivatized polyethyleneglycol, thiol-derivatized polyethyleneglycol, and any combination thereof.

In one embodiment, antigen-presenting cells and effector cells (including but not limited to, dendritic cells, macrophages, B cells, and T cells) are recruited to the device and activated to present antigens, autoantigens or allergens on their surfaces (antigen priming); the programmed immune cells can then migrate out of the device to downstream lymph nodes.

Preferably, the scaffold matrix has a porous structure and allows the ingress and egress of cells, such as bone marrow cells, splenocytes, and immune cells including, but not limited to, dendritic cells, macrophages, B cells, and T cells. The scaffold matrix allows extracellular delivery of pro-inflammatory or anti-inflammatory agents or adjuvants, antigens, autoantigens, or allergens, and therapeutic agents.

The scaffold matrix can have, for example, a size larger than cells, such as bone marrow cells, splenocytes, immune cells, such as, dendritic cells, macrophages, B cells, and T cells. In specific embodiments, the scaffold matrix has a diameter from 1 µm to 200 µcm, or any value therebetween. In specific embodiments, the pores of the scaffold matrix have a diameter from 0.5 µm to 20 µm, or any value therebetween.

In one embodiment, the pro-inflammatory agent of the invention enhances the immunogenicity of the antigen, autoantigen or allergen. The pro-inflammatory agent can be in a form of a pro-inflammatory adjuvant. Pro-inflammatory agents or adjuvants useful according to the present invention include, but are not limited to, aluminum hydroxide (Alum), lipopolysaccharides (LPS), cytosine-guanosine (CpG) oligonucleotide (CpG-ODN) sequences, polyinosinic:polycytidylic acid (poly IC), pro-inflammatory chemokines/cytokines such as IL-2, IL-4, IL-18, CpG rich oligonucleotides, leukotrienes such as leukotriene $A_4$ (LTA$_4$), leukotriene $B_4$ (LTB$_4$), leukotriene $C_4$ (LTC$_4$), leukotriene $D_4$ (LTD$_4$), leukotriene $E_4$ (LTE$_4$), arachidonic acids, prostaglandins, arachidonic acid-pathway activators, cyclo-oxygenase (COX, including COX-1 and/or COX-2)-pathway activators, incomplete Freund's adjuvant, complete Freund's adjuvant, and Freund's adjuvant with muramyldipeptide (MDP).

The anti-inflammatory agent used according to the invention suppresses inflammatory responses. In one embodiment, the anti-inflammatory agent is an anti-inflammatory adjuvant. Anti-inflammatory agents or adjuvants useful according to the present invention include, but are not limited to, hemoglobin:haptoglobin, heroin, heme:hemopexin, nonsteroidal anti-inflammatory drugs (NSAIDs) such as aspirin, ibuprofen, and naproxen, triterpinoids such as betulinic acid, bardoxolone methyl, and triterpenoid saponins, ethyl pyruvate (EP), hemeoxygenase (HO-1)-pathway activators, arachidonic acid-pathway inhibitors, and COX-pathway inhibitors.

In one embodiment, immuno-modulating molecules useful according to the present invention induce the migration of cells including, but not limited to, bone marrow cells, splenocytes, immune cells including antigen-presenting cells, such as, dendritic cells, macrophages, B cells, and T cells. In certain embodiments, the immuno-modulating molecule is a chemokine or chemoattractant such as, for example, CC chemokines such as CCL1, CCL2, CCL3, CCL4, CCL5, CCL6, CCL7, CCL8, CCL9, CCL10, CCL11, CCL12, CCL13, CCL14, CCL15, CCL16, CCL17, CCL18, CCL19, CCL20, CCL21, CCL22, CCL23, CCL24, CCL25, CCL26, CCL27, and CCL28, CXC chemokines, C chemokines, and CX$_3$C chemokines.

In one embodiment, the immuno-modulating molecule that induces the migration of an immune cell is selected from a granulocyte macrophage colony stimulating factor (GM-CSF) polypeptide or a granulocyte-colony stimulating factor (G-CSF) polypeptide. GM-CSF and G-CSF polypeptides useful according to the present invention can be isolated from endogenous sources, can be recombinantly produced, or can be chemically synthesized. In one embodiment, GM-CSF and/or G-CSF polypeptides are humanized derivatives of mammalian GM-CSF polypeptides. Exemplary mammalian species from which GM-CSF and G-CSF polypeptides can be derived include, but are not limited to, mice, rats, hamsters, and primates.

In one embodiment, the GM-CSF polypeptide useful according to the invention is a human GM-CSF having an amino acid sequence of SEQ ID NO: 1 (GenBank Accession No. AAA52578). In certain embodiments, GM-CSF polypeptides useful according to the present invention have at least 80%, 85%, 90%, 95%, or 99% identity to SEQ ID NO: 1. In one embodiment, the G-CSF polypeptide useful according to the invention is a human G-CSF having an amino acid sequence of SEQ ID NO: 2 (GenBank Accession No. ADI49832). In certain embodiments, G-CSF polypeptides useful according to the present invention have at least 80%, 85%, 90%, 95%, or 99% identity to SEQ ID NO: 2.

In one embodiment, antigens useful according to the present invention can be derived from living or non-living antigenic/immunogenic components of infectious pathogens against which a protective immune response is to be induced. The antigens useful according to the present invention can be derived from bacteria, viruses, fungi, or other pathogens such as, for example, pertussis, polio, hepatitis, measles, mumps, *rubella*, influenza, smallpox, zoster, anthrax, tetanus, rotavirus, rabies, chickenpox, meningococcus, diphtheria, anpapillomavirus, encephalitis, pneumococcus, pneumonia, typhus, typhoid fever, *streptococcus, staphylococcus, neisseria*, lyme disease, cholera, *E. coli, shigella, leishmania*, leprosy, cytomegalovirus (CMV), respiratory syncytial virus, Epstein Barr virus, herpes, parainfluenza, adenovirus, human immunodeficiency virus (HIV), varicella, yellow fever, flavivirus, dengue, toxoplasmosis, coccidiomycosis, schistosomiasis, malaria, *Chlamydia trachomatis, Chlamydia pneumonaie, M. tuberculosis*, and *H. pylori*.

In one embodiment, antigens useful according to the present invention are tumor or cancer antigens. Tumor or cancer antigens can be derived from non-malignant, malignant, or metastatic tumor/cancer cells against which protective immunity is to be induced. For example, tumor or cancer antigens can be derived from antigenic/immunogenic epitopes displayed on the surfaces of tumor and/or cancer cells. Exemplary embodiments of the tumor or cancer antigens of the present invention can be derived from breast, lung, colon, gastric, oral, esophagus, bone marrow, stomach, CNS, and liver carcinoma cells.

Autoantigens useful according to the present invention can be derived from endogenous antigenic peptides or peptide fragments capable of inducing unwanted auto-immune responses.

In the case of diabetes, the autoantigens useful according to the present invention can be, for example, insulin, glutamic acid decarboxylase (GAD), and insulinoma-associated-2-protein (IA-2).

In one embodiment, allergens useful according to the present invention can be proteins, peptides, nucleic acids, or other substances that trigger allergenic reactions. For example, allergens can be derived from proteins, peptides, nucleic acids, or otherwise innocuous substances of peanuts, sesame seeds, milk, wheat, and pollen.

In a further embodiment, the immuno-modulating device further comprises a nucleic acid that encodes an antigen, autoantigen, or allergen, or an antibody or auto-antibody that specifically binds to an antigen, autoantigen, or allergen useful according to the invention. In a specific embodiment, the scaffold matrix further comprises nucleic acids, antibodies, and/or auto-antibodies useful according to the invention. In one specific embodiment, the microparticle further encapsulates therein nucleic acids, antibodies, and/or auto-antibodies useful according to the invention.

"Specific binding" or "specificity" refers to the ability of antigen, antibody or other agent to exclusively bind to a target antigen, antibody, or other agent while having relatively little non-specific affinity with non-targets. Specificity can be determined by binding or competitive binding assays, using, e.g., Biacore instruments. Specificity can be mathematically calculated by, e.g., an about 10:1, about 20:1, about 50:1, about 100:1, 10.000:1 or greater ratio of affinity/avidity in binding to the specific target versus nonspecific binding to irrelevant molecules.

In one specific embodiment, the immuno-modulating device of the present invention comprises a scaffold matrix comprising an immune modulating molecule that induces the migration of a target immune cell, an adjuvant, a microparticle, and one or more additional therapeutic agents; wherein the outer surface of the microparticle comprises one or more surface ligands that bind to the target immune cell, and the microparticle encapsulates therein, at least an antigen, autoantigen, or allergen.

In one embodiment, the immuno-modulating device of the present invention comprises:
1) a pro-inflammatory composition comprising a biocompatible scaffold matrix, wherein the scaffold matrix comprises:
   a) an immuno-modulating molecule that induces the migration of an immune cell,
   b) a pro-inflammatory agent and/or adjuvant,
   c) a microparticle encapsulating therein, at least,
      i) an antigen, autoantigen, or allergen,
      ii) optionally, a pro-inflammatory agent or adjuvant, and,
      iii) optionally, one or more additional therapeutic agents, and
   d) optionally, one or more therapeutic agents; and
2) an anti-inflammatory composition comprising a scaffold matrix, wherein the scaffold matrix comprises:
   a) an anti-inflammatory agent or adjuvant,
   b) optionally, an immuno-modulating molecule that induces the migration of an immune cell,
   c) optionally, an antigen, autoantigen, or allergen,
   d) optionally, one or more additional therapeutic agents, and
   e) optionally, a microparticle encapsulating therein, at least,
      i) an antigen, autoantigen, or allergen,
      ii) optionally, an anti-inflammatory agent or adjuvant, and
      iii) optionally, one or more additional therapeutic agents.

In one embodiment, the scaffold matrix allows for the ingress and egress of cells, and cannot be phagocytosed. As a result, agents contained in the scaffold matrix can be released extracellularly. In one embodiment, the microparticle can be phagocytosed by immune cells. As a result, the agents encapsulated in the microparticle can be released inside the immune cells.

Additional therapeutic agents useful according the invention include, for example, immunomodulatory agents, transforming growth factor beta 1, rapamycin, vitamin D, and retinoic acid. Therapeutic agents can be hydrophilic or hydrophobic substances.

In preferred embodiments, the scaffold matrix and the microparticle are made of substantially biologically inert or biologically compatible materials. The terms "inert," "biologically inert" or "biologically compatible," as used herein, refer to a substance or material that, after the normal healing period when administered into living tissues, does not elicit substantially adverse biochemical, allergic, or unwanted immune responses. Preferably, the scaffold matrix and the microparticles are biodegradable.

In one embodiment, the outer surface of the microparticle comprises one or more surface ligands or surface antibodies that target specific immune cells. Preferably, the surface ligands or antibodies also induce apoptotic and/or tolerance-inducing pathways in immune cells. Exemplified surface ligands for dendritic cells include, but are not limited to, phosphatidyl serine (PS){PS receptor}, 4N1K {CD 36/CD 47}, PD2 {CD11c}, P2 {CD11b}, RGD{$\alpha_v\beta_3$}, and CS1{$\alpha_4\beta_7$}. In another embodiment, the surface antibody is an anti-DEC-205 antibody, which recognizes dendritic cells. In a preferred embodiment, the microparticle is surface modified with PD2 for targeting dendritic cells.

In one embodiment, the microparticle is smaller than immune cells (such as dendritic cells). In one embodiment, the microparticle is phagocytosable by immune cells (such as dendritic cells) and, thus, allows for intracellular delivery of therapeutic agents of interest. Phagocytosis allows for endosomal release of encapsulated antigens, autoantigens, and/or allergens from a polymeric matrix such as PLGA. In one embodiment, the microparticles generate both MHC-II-directed, as well as MHC-I-directed immune responses through cross-presentation.

The microparticle may have a diameter of 0.5 µm-10.0 µm, 0.5 µm-8.0 µm, 0.5 µm-5.0 µm, 0.5 µm-3.0 µm, 0.5 µm-2.0 µm, 0.5 µm-1.0 µm. In certain embodiments, the microparticle has a diameter of about 1.0 µm.

In one embodiment, the immuno-modulating device is formulated as an injectable vaccine formulation.

Methods for Modulating Immune Responses

Additional aspects of the invention provide methods for modulating an immune response in a subject by providing an initial artificial lymph-node environment, and a simultaneous, or subsequent, artificial spleen environment leading to the resolution of an activated immune response. Advantageously, the present invention provides a balanced, protective immunity against infections, cancer, allergy, and/or autoimmune diseases. In one specific embodiment, the present invention provides an improved vaccination useful for the prevention and/or treatment of type 1 diabetes.

In one embodiment, the method comprises administering, to a subject in need of such treatment, a pro-inflammatory adjuvant and an anti-inflammatory adjuvant, wherein the method further comprises administering an antigen, autoantigen or allergen, and an immuno-modulating molecule that induces the migration of an immune cell.

In one specific embodiment, the pro-inflammatory adjuvant and the anti-inflammatory adjuvant are administered simultaneously. In another specific embodiment, the anti-inflammatory adjuvant is administered after the administration of the pro-inflammatory adjuvant.

In a further embodiment, the method further comprises, administering a nucleic acid that encodes an antigen, autoantigen, or allergen, or an antibody or auto-antibody that specifically binds to an antigen, autoantigen, or allergen useful according to the invention.

In one embodiment, the method for modulating immune responses comprises:
1) administering a biocompatible scaffold matrix comprising an effective amount of a pro-inflammatory composition, wherein the pro-inflammatory composition comprises a pro-inflammatory agent or adjuvant, an antigen, autoantigen, or allergen, and an immuno-modulating molecule that induces the migration of an immune cell; and
2) administering a biocompatible scaffold matrix comprising an effective amount of an anti-inflammatory composition, wherein the anti-inflammatory composition comprises an anti-inflammatory agent or adjuvant.

In one embodiment, the method for modulating immune responses comprises:

1) administering a pro-inflammatory composition comprising a scaffold matrix comprising:
   a) an immuno-modulating molecule that induces the migration of an immune cell,
   b) a pro-inflammatory agent and/or adjuvant,
   c) a microparticle encapsulating therein, at least,
      i) an antigen, autoantigen, or allergen,
      ii) optionally, a pro-inflammatory agent or adjuvant, and,
      iii) optionally, one or more additional therapeutic agents, and
   d) optionally, one or more therapeutic agents; and
2) administering an anti-inflammatory composition comprising a scaffold matrix comprising:
   a) an anti-inflammatory agent or adjuvant,
   b) optionally, an immuno-modulating molecule that induces the migration of an immune cell,
   c) optionally, an antigen, autoantigen, or allergen,
   d) optionally, one or more additional therapeutic agents, and
   e) optionally, a microparticle encapsulating therein, at least,
      i) an antigen, autoantigen, or allergen,
      ii) optionally, an anti-inflammatory agent or adjuvant, and,
      iii) optionally, one or more additional therapeutic agents.

In a preferred embodiment, the scaffold matrix is made of biocompatible material comprising hydrogel. In a preferred embodiment, the microparticle is made of material comprising poly(lactic-co-glycolic acid) (PLGA). In one embodiment, the immuno-modulating molecule that induces the migration of an immune cell is selected from GM-CSF, G-CSF, or both.

In one embodiment, the immuno-modulating device/composition is administered via injection.

Prevention and/or Treatment of Diseases

The present invention also provides methods for the prevention, treatment, or amelioration of pathogenic infections, cancer, allergy, and/or autoimmune diseases. The method comprises administering, to a subject in need of such treatment, an effective amount of an immuno-modulating device or composition of the present invention. In one specific embodiment, the present invention can be used to prevent and/or treat type 1 diabetes.

The term "treatment" or any grammatical variation thereof (e.g., treat, treating, and treatment etc.), as used herein, includes but is not limited to, ameliorating or alleviating a symptom of a disease or condition, reducing, suppressing, inhibiting, lessening, or affecting the progression, severity, and/or scope of a condition.

The term "prevention" or any grammatical variation thereof (e.g., prevent, preventing, and prevention etc.), as used herein, includes but is not limited to, delaying the onset of symptoms, preventing relapse to a disease, decreasing the number or frequency of relapse episodes, increasing latency between symptomatic episodes, or a combination thereof.

The term "effective amount," as used herein, refers to an amount that is capable of treating or ameliorating a disease or condition or otherwise capable of producing an intended therapeutic effect.

In one embodiment, the treatment effects of allergy, immune disorders or auto-immune diseases can be determined by the recall response, which is known in the art. The recall response can be measured either by antibody titer, the degree of T cell proliferation, and/or the amount of cytokine release, in response to a second encounter of the antigenic stimulus. For example, in the autoimmunity field, it is common to measure the proliferation of regulatory T cells (Treg), anergic T cells, deletion of T cells, as the readout post "tolerogenic vaccination". In one embodiment, after the subject is treated with an antigen, autoantigen, or allergen in accordance with the present invention, the subject acquires protective immunity against that antigen, autoantigen, or allergen; therefore, the second encounter with the antigen, autoantigen, or allergen post-immunity (either from natural infection or vaccine) is mild, quiescent and largely asymptomatic (somewhat analogous to that of regulated, Treg mediated response). In one embodiment, in a subject treated in accordance with the present invention, the second encounter with the antigen, autoantigen, or allergen produces reduced antibody titer, reduced T cell proliferation, and/or reduced cytokine release.

The term "subject," as used herein, describes an organism, including mammals such as primates, to which treatment with the compositions according to the present invention can be provided. Mammalian species that can benefit from the disclosed methods of treatment include, but are not limited to, apes, chimpanzees, orangutans, humans, monkeys; and domesticated animals such as dogs, cats, horses, cattle, pigs, sheep, goats, chickens, mice, rats, guinea pigs, and hamsters.

In one embodiment, the present invention can be used in the prevention, treatment or amelioration of infection, inflammation, allergenic reactions, diseases associated with pathological cell proliferation, neoangiogenesis, and malignancy.

In one embodiment, the present invention can be used in the prevention, treatment or amelioration of pathogenic infections caused by bacteria, viruses, fungi, protozoa, and other microorganisms. In one embodiment, the present invention can be used to vaccinate against pathogenic infections. Exemplary embodiments of the infections that can be prevented or treated by the present invention include, but are not limited to, infections by pertussis, polio, hepatitis, measles, mumps, *rubella*, influenza, smallpox, zoster, anthrax, tetanus, rotavirus, rabies, chickenpox, meningococcus, diphtheria, anpapillomavirus, encephalitis, pneumococcus, pneumonia, typhus, typhoid fever, *streptococcus, staphylococcus, neisseria*, lyme disease, cholera, *E. coli, shigella, leishmania*, leprosy, cytomegalovirus (CMV), respiratory syncytial virus, Epstein Barr virus, herpes, parainfluenza, adenovirus, human immunodeficiency virus (HIV), varicella, yellow fever, flavivirus, dengue, toxoplasmosis, coccidiomycosis, schistosomiasis, malaria, *Chlamydia trachomatis, Chlamydia pneumoniae, M tuberculosis*, and *H. pylori*.

In one embodiment, the present invention can be used in the prevention, treatment or amelioration of cancer. In one embodiment, the present invention can be used to immunize against cancer. Exemplary embodiments of cancer or carcinoma types that can be prevented or treated by the present invention include, but are not limited to, breast, lung, colon, gastric, oral, esophagus, bone marrow, stomach, CNS, and liver cancer.

In one embodiment, the present invention can be used in the prevention, treatment or amelioration of allergies or allergenic reactions.

In one embodiment, the present invention can be used in the prevention, treatment or amelioration of immune disorders and/or autoimmune diseases, particularly, type 1 diabetes. In certain embodiments, the present invention is useful to treat or ameliorate immune disorders and autoimmune diseases including, but not limited to, type 1 diabetes, rheumatoid arthritis, Crohn's disease, chronic inflammatory bowel diseases, graft-versus-host and transplant rejection, rheumatoid arthritis, celiac disease, *pemphigus vulgaris*, asthma, rhinitis, chronic urticaria, atopic dermatitis, systemic lupus erythematosus (SLE), and related disorders.

Formulations and Administration

The present invention provides for pharmaceutical compositions. In one embodiment, the composition comprises a therapeutically effective amount of a device or composition of the present invention and, optionally, a pharmaceutically acceptable carrier.

In one embodiment, the devices and compositions of the present invention are formulated into a vaccine composition for administration to subjects having certain risks of developing infections, cancer, allergies and/or autoimmune-related disorders. A vaccine composition is an antigenic preparation that comprises one or more immunogenic antigens used to produce active immunity to a disease. In addition, the compositions of the present invention can be administered to a subject with existing diseases or symptoms of infections, cancer, allergy or allergenic reactions, and inflammatory and autoimmune-related disorders, and provides for customized vaccine schedules and compositions to prevent or minimize worsening of the diseases.

The compositions of the subject invention can be administered to the subject being treated by standard routes, including oral, inhalation, or parenteral administration including intravenous, subcutaneous, topical, transdermal, intradermal, transmucosal, intraperitoneal, intramuscular, intracapsular, intraorbital, intracardiac, transtracheal, subcutaneous, subcuticular, intraarticular, subcapsular, subarachnoid, intraspinal, epidural and intrasternal injection, infusion, and electroporation, as well as co-administration as a component of any medical device or object to be inserted (temporarily or permanently) into a subject.

In one embodiment, the device and composition of the present invention are formulated as an injectable formulation. In certain specific embodiments, the device and composition is administered by routes including, but not limited to, subcutaneous injection, intradermal injection, and intramuscular injection. In one embodiment, the device of the present invention can be implanted or affixed to tissues of a subject.

Suitable non-toxic pharmaceutically acceptable carriers for use with the agent will be apparent to those skilled in the art of pharmaceutical formulation. See, for example, *Remington's Pharmaceutical Sciences*, seventeenth edition, ed. Alfonso R. Gennaro, Mack Publishing Company, Easton, Pa. (1985).

The therapeutic dosage range of the antigens, autoantigens, allergens and adjuvants can be determined by one skilled in the art having the benefit of the current disclosure. Naturally, such therapeutic dosage ranges will vary with the size, species and physical condition of the patient, the severity of the patient's medical condition, the particular dosage form employed, the route of administration and the like.

The composition can be administered in a single dose or in more than one dose over a period of time to confer the desired effect.

In a preferred embodiment, the device and composition of the present invention can be formulated for parenteral administration. The preparation of an aqueous composition that contains one or more agents, such as a genetic construct of the present invention, will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi.

Sterile injectable solutions are prepared by incorporating the active compounds in the required amount in the appropriate solvent followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum drying and freeze-drying techniques, which yield a powder of the active ingredient, plus any additional desired ingredient from a previously sterile-filtered solution thereof.

When administering more than one, the administration of the agents can occur simultaneously or sequentially in time. The agents can be administered before and after one another, or at the same time. The methods also include co-administration with other drugs that are used to treat retinopathy or other diseases described herein.

Following are examples that illustrate procedures for practicing the invention. This example should not be construed as limiting. All percentages are by weight and all solvent mixture proportions are by volume unless otherwise noted.

EXAMPLE 1

This Example pertains to the prevention and/or treatment of type 1 diabetes by autoantigen presentation via the injection of an adjuvant-modified hydrogel-based matrix, containing antigens/antigenic peptides and a chemoattractant.

Specifically, a biodegradable, phagocytosable microparticle (MP) made of D,L-lactic acid-co-glycolic acid (PLGA) was used to deliver therapeutic compositions comprising Insulin B chain: 9-23 and an adjuvant selected from CpG ODN 1826 or hemoglobin:haptoglobin (Hb:Hp). The MPs were placed into a hydrogel that contains GM-CSF—a chemoattractant.

The vaccine composition was injected subcutaneously into 12-week old female non-obese diabetic (NOD) mice. The mice were divided into the following groups (10 mice/group): a) untreated mice; b) mice treated with hydrogels containing GM-CSF and empty MPs; c) mice treated with hydrogels containing GM-CSF and MPs loaded with B-9-23; d) mice treated with hydrogels containing GM-CSF and MPs loaded with CpG and B-9-23; e) mice treated with hydrogels containing GM-CSF and MPs loaded with Hb:Hp and B9-23; f) mice treated with hydrogels containing GM-CSF and MPs loaded with CpG; and g) mice treated with hydrogels containing GM-CSF and MPs loaded with Hb:Hp.

Blood glucose level was measured once a week until the end of week 32. Kaplan Meier analysis revealed a p-value of 0.0636 in terms of survival proportions.

Mice with the highest survival include those treated with hydrogel-based compositions containing GM-CSF or hydrogel-based compositions containing GM-CSF and MPs loaded with CpG ODN 1826 (40% of survival proportions versus 0% of untreated animals).

An in vitro migration assay was performed to evaluate the migratory capacity of splenocytes and bone marrow cells toward GM-CSF. NOD, non-obese resistant (NOR), and C57/BL6 (n=3 per group) mouse cells were used in this assay. After 24 hrs, in the presence of GM-CSF, whole bone marrow cells and splenocytes of C57/BL6 and NOR mice showed a 100% increase in cell migration. While NOD bone marrow cells migrated in a similar manner as NOR and C57/BL6 bone marrow cells, NOD splenocytes showed no difference in migration ratios with or without GM-CSF (p<0.05).

This indicates that T1D is associated with a peripheral migration defect, and this peripheral migration defect can be treated by improving bone marrow mobilization prior to immunomodulation therapies. In addition, the administration of a bone marrow mobilizing agent (such as G-CSF) together with immunosuppressive agents (such as Anti Thymocyte Globulin or anti-CD3) produces a synergistic effect in T1D treatment.

EXAMPLE 2

A controlled release of antigen and immunomodulatory factors was effected through an injectable microparticles/hydrogel system.

Poly D, L-lactic acid-co-glycolic acid microparticles (MP) were used as a phagocytosable delivery vehicle for denatured human insulin (25 μg insulin/mg MP, 5 mg MP/injection). The MP were mixed with a hydrogel containing the chemoattractant GM-CSF and the adjuvants CpG ODN 1826 (CpG) and/or hemoglobin:haptoglobin (Hb:Hp). CpG induces inflammatory pathways, while Hb:Hp is bound by CD163, a scavenger receptor, and induces HO-1 and IL-10.

These formulations were injected subcutaneously into 8 wk old female NOD mice (n=10/group). Three injections, two weeks apart, were given to all mice.

Groups consisted of GM-CSF with empty MP, GM-CSF/CpG/Hb:Hp with empty MP, GM-CSF/CpG with insulin MP, GM-CSF/Hb:Hp with insulin MP, and GM-CSF/CpG/Hb:Hp with insulin MP.

Figure 2:
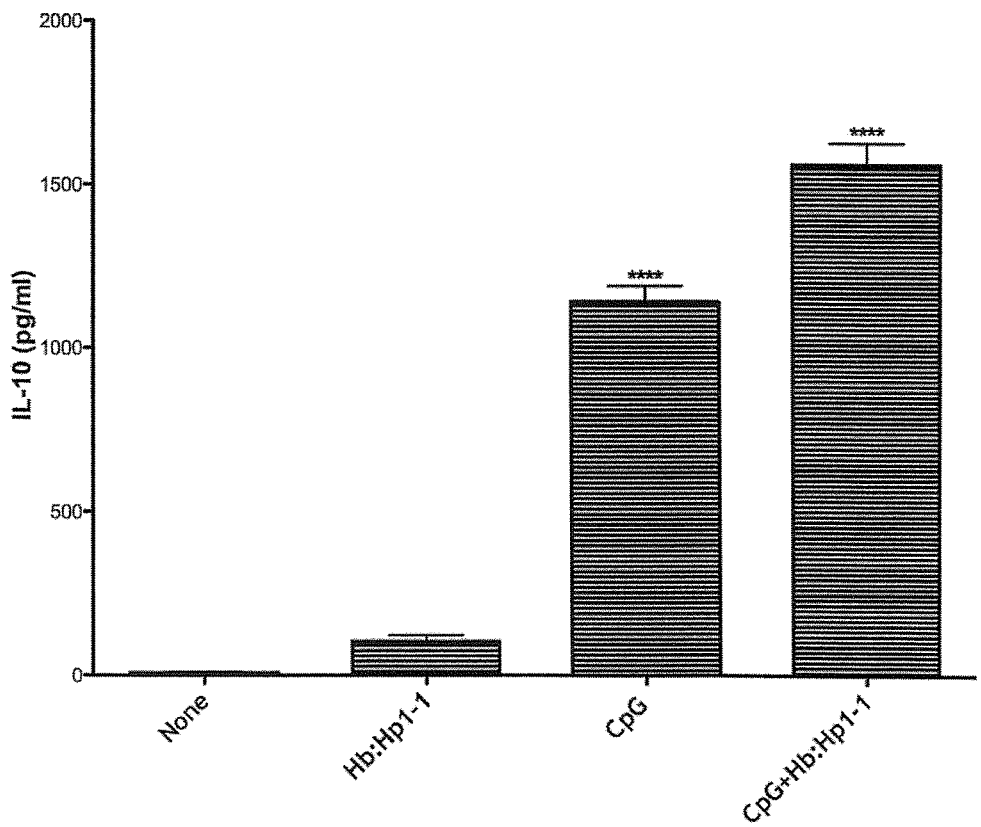
FIG. 2 shows the effect of adjuvant stimulation on IL-10 production from mice splenocytes. Splenocytes from the surviving mice produced significantly higher levels of IL-10 when cells were stimulated with either CpG alone or combination of CpG and Hb:Hp. [28 weeks old, n=5, ANOVA, ****P<0.0001]

Results of these experiments are shown in FIGS. 1 and 2.

Blood glucose (BG) values were determined once per week until 28 weeks of age. Diabetes was diagnosed when BG was higher than 250 mg/dL on two consecutive days.

The group treated with GM-CSF/CpG/Hb:Hp with insulin MP had the largest proportion of animals that remained euglycemic (50% vs 10% in the control group; p=0.0199, Kaplan-Meier).

Mechanistically, CpG-treated or CpG/Hb:Hp-treated splenocytes from untreated NOD mice produced significantly higher levels of IL-10 than untreated or Hb:Hp treated splenocytes (n=3, ***P<0.001). This synergism suggests that activation of cells is necessary to engage the HO-1 pathway.

Our novel enhancement of the HO-1/IL-10 pathway post-activation may contribute to both resolution of inflammation and tolerance induction.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

---

We claim:

1. A method for inducing a protective immune response against a target autoantigen, wherein the method comprises administering, to a subject in need of such an immune response, a pro-inflammatory adjuvant and an anti-inflammatory adjuvant, wherein said method further comprises administering the target autoantigen;
    wherein the pro-inflammatory adjuvant comprises one or more of the following: cytosine-guanosine (CpG) oligonucleotide (CpG-ODN) sequences, a CpG rich oligonucleotide, incomplete Freund's adjuvant, complete Freund's adjuvant, and Freund's adjuvant with muramyldipeptide (MDP);
    wherein the anti-inflammatory adjuvant comprises one or more of the following: hemoglobin:haptoglobin, hemin, heme:hemopexin, ethyl pyruvate (EP), anti Thymocyte Globulin, and anti-CD3; and
    wherein the target autoantigen is an autoantigen of Type 1 diabetes selected from insulin, proinsulin, the B chain of insulin, glutamic acid decarboxylase (GAD), and insulinoma associated-2-protein (IA-2).

2. The method, according to claim 1, wherein the anti-inflammatory adjuvant comprises one or more of the following: hemoglobin:haptoglobin, hemin, and ethyl pyruvate (EP).

3. The method, according to claim 1, wherein the anti-inflammatory adjuvant is administered after the pro-inflammatory adjuvant.

4. The method, according to claim 1, wherein the pro-inflammatory adjuvant and the anti-inflammatory adjuvant are administered simultaneously.

5. The method, according to claim 1, further comprising administering an immuno-modulating molecule that induces the migration of an immune cell.

6. The method, according to claim 5, wherein the immuno-modulating molecule is selected from GM-CSF, G-CSF, or both.

* * * * *

SEQUENCE LISTING

```
<160> NUMBER OF SEQ ID NOS: 2

<210> SEQ ID NO 1
<211> LENGTH: 144
<212> TYPE: PRT
<213> ORGANISM: Homo sapiens

<400> SEQUENCE: 1

Met Trp Leu Gln Ser Leu Leu Leu Gly Thr Val Ala Cys Ser Ile
1               5                   10                  15

Ser Ala Pro Ala Arg Ser Pro Ser Pro Ser Thr Gln Pro Trp Glu His
            20                  25                  30

Val Asn Ala Ile Gln Glu Ala Arg Arg Leu Leu Asn Leu Ser Arg Asp
        35                  40                  45

Thr Ala Ala Glu Met Asn Glu Thr Val Glu Val Ile Ser Glu Met Phe
    50                  55                  60

Asp Leu Gln Glu Pro Thr Cys Leu Gln Thr Arg Leu Glu Leu Tyr Lys
65                  70                  75                  80

Gln Gly Leu Arg Gly Ser Leu Thr Lys Leu Lys Gly Pro Leu Thr Met
                85                  90                  95

Met Ala Ser His Tyr Lys Gln His Cys Pro Pro Thr Pro Glu Thr Ser
            100                 105                 110

Cys Ala Thr Gln Ile Ile Thr Phe Glu Ser Phe Lys Glu Asn Leu Lys
```

-continued

```
            115                 120                 125
Asp Phe Leu Leu Val Ile Pro Phe Asp Cys Trp Glu Pro Val Gln Glu
        130                 135                 140

<210> SEQ ID NO 2
<211> LENGTH: 138
<212> TYPE: PRT
<213> ORGANISM: Homo sapiens

<400> SEQUENCE: 2

Thr Pro Leu Gly Pro Ala Ser Ser Leu Pro Gln Ser Phe Leu Leu Lys
1               5                   10                  15

Cys Leu Glu Gln Val Arg Lys Ile Gln Gly Asp Gly Ala Ala Leu Gln
            20                  25                  30

Glu Lys Leu Ala Gly Cys Leu Ser Gln Leu His Ser Gly Leu Phe Leu
        35                  40                  45

Tyr Gln Gly Leu Leu Gln Ala Leu Glu Gly Ile Ser Pro Glu Leu Gly
    50                  55                  60

Pro Thr Leu Asp Thr Leu Gln Leu Asp Val Ala Asp Phe Ala Thr Thr
65                  70                  75                  80

Ile Trp Gln Gln Met Glu Glu Leu Gly Met Ala Pro Ala Leu Gln Pro
                85                  90                  95

Thr Gln Gly Ala Met Pro Ala Phe Ala Ser Ala Phe Gln Arg Arg Ala
            100                 105                 110

Gly Gly Val Leu Val Ala Ser His Leu Gln Ser Phe Leu Glu Val Ser
        115                 120                 125

Tyr Arg Val Leu Arg His Leu Ala Gln Pro
    130                 135
```